United States Patent [19]

Ostlind et al.

[11] Patent Number: 5,017,603
[45] Date of Patent: May 21, 1991

[54] XANTHOMEGNIN, A KNOWN COMPOUND, IS AN ANTIPARASITIC AGENT

[75] Inventors: Dan A. Ostlind, Bound Brook, N.J.; Sagrario Mochales, Madrid, Spain

[73] Assignee: Merck & Co., Inc., Rahway, N.J.

[21] Appl. No.: 496,738

[22] Filed: Mar. 21, 1990

[51] Int. Cl.$^5$ ................... A01N 43/16; A01N 43/08
[52] U.S. Cl. .............................. 514/455; 514/468
[58] Field of Search ...................... 514/453, 468

[56] References Cited

U.S. PATENT DOCUMENTS

| | | | |
|---|---|---|---|
| 4,414,226 | 11/1983 | Ikushima et al. | 424/279 |
| 4,530,845 | 7/1985 | Ikushima et al. | 514/453 |
| 4,639,467 | 1/1987 | Celino et al. | 514/468 |
| 4,837,399 | 6/1989 | Baker et al. | 514/468 |
| 4,839,382 | 6/1989 | Maestrone et al. | 514/453 |
| 4,927,848 | 5/1990 | Konishi et al. | 514/453 |

FOREIGN PATENT DOCUMENTS 016452  9/1979  Japan ................................. 514/453

OTHER PUBLICATIONS

Ito, Y., et al., *Biochemical Studies of Pigments from the Pathogenic Fungus*, Microsporum cookei, J. Biochem., 74, pp. 805–900, 1973.

Just, G., and Day, W., *Metabolites of Pathogenic Fungi III., The Structure of Xanthomegnin*, Can, J. Chem., 41, pp. 74–79, 1963.

Wirth, J. C., et al., *The Isolation of Xanthomegnin From Several Strains of The Dermatophyte Trichophyton Rubrum*, Phytochemistry, 4, pp. 505–509, 1965.

Stack, M. E., et al., Isolation and Identification of Xanthomegnin, Viomellin, Rubrosulphin, and Viopurpurin as Metabolites of Penicillium viridicatum, Appl. Env. Microbiol., 33, pp. 351–355, 1977.

Peterson, R. E., and Grove, M. D., Isolation of Xanthomegnin from *Penicillium viridicatum*, by Preparative High-Pressure Liquid Chromatography, App. Env. Microbiol., 45, pp. 1937–1938, 1983.

Kawai, K. et al., Effects of Xanthomegnin and Duclauxin on Culture Cells of Murine Leukemia and Ehrlich Ascitic Tumor, Res. Com. Chem. Path. Pharm., 36, pp. 429–438, 1982.

*Primary Examiner*—Frederick E. Waddell
*Assistant Examiner*—Theodore J. Criares
*Attorney, Agent, or Firm*—Hesna J. Pfeiffer; Raymond M. Speer; Robert J. North

[57] ABSTRACT

The controlled aerobic fermentation of the fungal organism *Fusarium lateritium* var. longum produces xanthomegnin. Xanthomegnin has been discovered to have potent parasiticidal, anthelminthic, and insecticidal activity.

2 Claims, No Drawings

XANTHOMEGNIN, A KNOWN COMPOUND, IS AN ANTIPARASITIC AGENT

BACKGROUND OF THE INVENTION

Xanthomegnin was originally reported to be isolated from several species of each of the genera *Penicillium*, *Aspergillus* and *Trichophyton*. Isolation of xanthomegnin from *Trichophyton rubrum* was reported by J. C. Wirth et. al., Phytochemistry, 1965, Vol. 4, pp 505–509 and from *T. meznini* as reported by G. Just et al., Can. J. Chem., 41, 74, 1963. The present invention describes the production of xanthomegnin from a species of fungus of the genus *Fusarium*. Organisms of this genus have not been previously known to produce xanthomegnin. Xanthomegnin has been determined by G. Just et al. to have the chemical structure of Formula I:

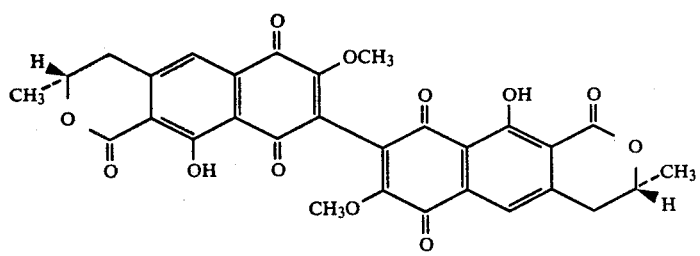

It may also be identified by the chemical name (−)3,3′-bis[2-methoxy-5-hydroxy-7-(2-hydroxypropyl)-8-carboxy-1, 4-naphthoquinone lactone].

Xanthomegnin has been shown to have limited antibacterial activity (Boutibonnes, O. et al, Mycopathologia, 87 (1–2), 43 49, 1984). Xanthomegnin has also been tested with minimal success, as an antitumor agent (Kawai, K., et al, Res. Commun. Chem. Pathol. Pharmacol., 36(3), 429–438, 1982). This experiment demonstrated that xanthomegnin had growth inhibitory effects in vitro against certain tumor cells. However, when xanthomegnin was administered intraperitoneally to mice bearing tumor cells, no tumor growth inhibition was seen. Due to the lack of success in the use of xanthomegnin as an antibacterial or antitumor agent, investigation of xanthomegnins' biological properties diminished.

According to the present invention, xanthomegnin has been discovered to have potent parasiticidal, anthelminthic, and insecticidal activity against organisms which affect human and animal health.

OBJECTS OF THE INVENTION

It is an object of the present invention to provide a novel use as an antiparasitic and insecticide, in particular as an anthelminthic, acaricidal and trematocidal agent, for the known compound xanthomegnin. It is therefore an additional object of the present invention to provide antiparasitic and insecticidal compositions containing xanthomegnin. These and other obJects of the present invention will be apparent from the following description.

SUMMARY OF THE INVENTION

It has now been discovered that the known compound xanthomegnin, which is produced by certain fungal organisms, has antiparasitic, anthelminthic, and insecticidal activity.

DETAILED DESCRIPTION OF THE INVENTION

Xanthomegnin, was originally reported to be isolated from several species of each of the genera *Penicillium*, *Aspergillus* and *Trichophyton*. Isolation of xanthomegnin from *Trichophyton rubrum* was reported by J. C. Wirth et. al , Phytochemistry, 1965, Vol. 4, pp 505–509 and from *T. megnini* as reported by G. Just et al., Can. J. Chem., 41, 74, 1963. The present invention describes the production of xanthomegnin from a culture of a fungal species of the genus Fusarium. The organism was identified as *Fusarium lateritium* var. *longum*. Organisms of this genus have not been previously known to produce xanthomegnin. The culture is designated MF5071 WT in the culture collection of Merck & Co., Inc., Rahway, N.J. A sample of this culture, capable of producing xanthomegnin, has been deposited, without restriction as to availability, in the permanent culture collection of the American Type Culture Collection at 301 Parklawn Drive, Rockville, MD. 20852, and has been assigned the accession number ATCC No. 20959.

The morphological and cultural characteristics of ATCC 20959 are described below: On potato dextrose agar at 22–24° C., colonies grow rapidly, attaining a diameter of 40–45 mm in about 5 days. At first the colonies are straw yellow to mustard yellow and with age become mineral red to dark mineral red. Aerial hyphae form on potato dextrose agar, but not on cornmeal or hay extract agar, and are light corinthian red to corinthian red.

Color designations are taken from Color Standards And Nomenclature, R. Ridgway, 1912.

Conidiogenous cells are either solitary or small, branched clusters of phialides, about $10-22 \times 4-7\mu$ diameter, with a single apical pore. Macroconidia are hyaline, fusoid to lanceolate, straight to slightly curved, with a narrow, acicular to acumunate, slightly curved terminal cell, with a pedicellate basal cell, 3–11 septate but usually 5–9 septate, about $35-115\mu \times 5-9.5\mu$. Microconidia are absent. Chlamydospores are observed after about 2 weeks in culture, are infrequent, subglobose to pyriform, sometimes with an apical papilla at either terminal, and associated with groups of phialides or intercalary, about $10-22\mu$ diameter, and are thin walled, hyaline to pale brown. Hyphae are septate, branched, up to $8\mu$ in diameter, and are hyaline to grayish red to brownish red.

It should be noted that the media described hereinbelow are merely illustrative of the wide variety of media which may be employed, and are not intended to be limitative.

Fermentation was done by inoculating a frozen vial of MF5071 WT (ATCC 20959) into 50 ml of autoclaved growth medium I in an unbaffled Erlenmeyer flask. After about 3 days of incubation at 28° C. with agitation at 212 rpm, a 2 ml portion of this growth was used to inoculate 18 unbaffled, 250 ml Erlenmeyer flasks each containing twice autoclaved growth medium II. These flasks were incubated for 7 days without agitation at 25° C., followed by 8 days at 25° C. with agitation at 220 rpm. The volume in each flask was then adjusted to about 20–25 ml by adding water, followed by the addition of methanol to a final methanol concentration of about 50%, yielding a final volume of about 40–50 ml.

| Medium I: | |
|---|---|
| INGREDIENT | PER LITER OF WATER |
| corn steep liquor | 5.0 g |
| tomato paste | 40.0 g |
| oat flour | 10.0 g |
| glucose | 10.0 g |
| trace element mix | 10.0 ml |

| Trace Element Mix: | |
|---|---|
| INGREDIENT | PER LITER OF WATER |
| $FeSO_4 \cdot 7H_2O$ | 1.0 g |
| $MnSO_4 \cdot 4H_2O$ | 1.0 g |
| $CuCl_2 \cdot 2H_2O$ | 0.025 g |
| $CaCl_2$ | 0.1 g |
| $H_3BO_3$ | 0.056 g |
| $(NH_4)_6Mo_7O_{24}$ | 0.019 g |
| $ZnSO_4 \cdot 7H_2O$ | 0.2 g |

| Medium II: | |
|---|---|
| INGREDIENT: | PER 20 ml OF WATER |
| millet | 15.0 g |
| yeast extract | 0.5 g |
| Na tartrate | 0.1 g |
| $FeSO_4 \cdot 7H_2O$ | 0.01 g |
| sucrose | 0.5 g |
| alfalfa | 0.5 g |
| corn oil | 0.1 ml |

The methanol extracted fermentation broth from MF5071-WT (ATCC 20959) was lyophilized, and dissolved in water prior to use int he antiparasitic assays described in Examples I and II. Xanthomegnin was isolated and identified in the fermentation broths by comparison to published data according to methods well known in the art (Wirth, J.C., et al., ibid). Fifteen 250 ml flasks, each containing 40 ml of Medium II (600 ml total) of the static fungal culture were combined and extracted with 1.0L of ethyl acetate by mixing in a Waring blender for 20 minutes. The puree was filtered through sintered glass. The residue was again extracted with 1.0L of ethyl acetate and filtered through sintered glass. The combined filtrates were concentrated to a volume of 600 ml. This aqueous concentrate was extracted three time with equal volumes of hexanes in a separatory funnel. The aqueous ethyl acetate phase was evaporated to dryness and provided 1.5 g of residue. 816mg of this residue was dissolved in 10 ml of methylene chloride and applied to a silica column (silcas cc7, 250 ml in methylene chloride). The column was washed with 200 ml of methylene chloride and developed with a gradient of ethyl acetate (0 to 100% in methylene chloride). Fractions were stored at 4° C. for 14 days, during which an orange precipitate formed in the biologically active fractions. Fractions with biological activity were pooled and filtered through sintered glass. The orange solid was washed several times with cold ethyl acetate and dried, providing about 240mg of product. This product was Judged to be greater than 95% pure by thin layer chromatography and high pressure liquid chromatography. This product was identified as xanthomegnin by mass spectroscopy, and $^1H$ and $^{13}C$ nuclear magnetic resonance.

According to the present invention, it has been discovered that xanthomegnin is an effective antiparasitic agent useful for the control of parasites infecting humans, livestock and other animals as well as poultry and other birds. The novel compound of this invention has significant parasiticidal activity as an anthelmintic, insecticide and acaricide, in human and animal health and in agriculture.

The disease or group of diseases described generally as helminthiasis is due to infection of an animal host with parasitic worms known as helminths. Helminthiasis is common in humans and is a prevalent, serious economic problem in domesticated animals such as swine, sheep, horses, cattle, goats, dogs, cats and poultry. Among the helminths, the group of worms described as trematodes causes widespread and often times serious infection in various species of animals including humans. The most common genera of trematodes infecting the animals referred to above are Fasciola, Fasciolopsis, Heterophyes, Metagonimus, Parazonimus, Clonorchis, Episthorchis, Troglotrema, and Schistosoma.

The parasitic infections known as helminthiasis lead to anemia, malnutrition, weakness, weight loss, severe damage to the walls of the intestinal tract and other tissues and organs and, if left untreated, may result in death of the infected host. The instant compound has unexpectedly high activity against these parasites, and in addition is active against arthropod ectoparasites of animals and birds such as ticks, mites, lice, fleas, blowfly (in sheep Lucilia sp.), biting insects and such migrating dipterous larvae as Hyroderma sp. in cattle, Gastrophilus in horses, and Cuterebra sp. in rodents.

The instant comPound is also useful against parasites which infect humans. In addition to the trematodes, other common genera of parasites of the gastro-intestinal tract of man are nematodes such as Ancylostoma, Necator, Ascaris, Strongyloides, Trichinella, Capillaria, erichuris, and Enterobius, and cestodes (tapeworms) such as Diphyllobothrium, Taenia, Hymenolepis, and Echinococcus. Other medically important genera of nematode parasites which are found in the blood or other tissues and organs outside of the gastro intestinal tract are the filiarial worms such as Wuchereria, Brugia, Onchocerca, Loa, Dipetalonema, Mansonella, and Dracunculus and extra-intestinal stages of the intestinal worms Strongyloides and Trichinella. The compound is also of value against arthropods parasitizing man, biting insects and other dipterous pests causing annoyance to man.

The instant compound is also active against household pests such as the cockroach (Blatella sp.), clothes moth (Tineola sp.), carpet beetle (Attagenus sp.), and the housefly *Musca domestica*.

The instant compound is also useful against insect pests of stored grains such as Tribolium sp., Tenebrio sp. and of agricultural plants such as spider mites, (Tetranychus sp.), aphids (Acyrthiosidhon), migratory orthopterans such as locusts, and immature stages of insects living on plant tissue. The compound is useful as a nematocide for the control of soil nematodes and plant parasites such as Meloidogyne spp., which may be of importance to agriculture.

The instant compound may be administered orally in a unit dosage form such as a capsule, bolus or tablet, or as a liquid drench when used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or dicalcium phosphate.

Where it is desired to administer the instant compound in a dry, solid unit dosage form, capsules, boluses or tablets containing the desired amount of active compound usually are employed. These dosage forms are prepared by intimately and uniformly mixing the active ingredient with suitable finely divided diluents, filler, disintegrating agents and/or binders such as starch, lactose, talc, magnesium stearate, vegetable gums and the like. Such unit dosage formulations may be varied widely with respect the their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compound of the present invention may be administered to animals parenterally, for example, by intraruminal, intramuscular, intratracheal, or subcutaneous inJection in which event the active ingredient is dissolved or dispersed in a liquid carrier vehicle. For parenteral administration, the active material is suitably admixed with an acceptable vehicle, preferably of the vegetable oil variety su:h as peanut oil, cotton seed oil and the like. Other parenteral vehicles such as organic preparations using solketal, glycerol, formal and aqueous parenteral formulations are also used. The active compound is dissolved or suspended in the parenteral formulations generally containing from 0 005 to 5% by weight of the active compound.

Although the antiparasitic agent of this invention finds its primary use in the treatment and/or prevention of helminthiasis, it is also useful in the prevention and treatment of diseases caused by other parasites, for example, arthropod parasites such as ticks, lice, fleas, mites and other biting insects in domesticated animals and poultry. It is also effective in treatment of parasitic diseases that occur in other animals including humans. The optimum amount to be employed for best results will, of course, depend upon the species of animal to be treated and the type and severity of parasitic infection or infestation. Generally, good results are obtained with xanthomegnin by the oral administration of about 0.001 to 100 mg per kg of animal body weight, such total dose being given at one time or in divided doses over a relatively short period of time such as 1-5 days. Excellent control of such parasites is obtained in animals by administering about 0.1 to 100 mg per kg of body weight in a single dose. Repeat treatments are given as required to combat re infections and are dependent upon the species of parasite and the husbandry techniques being employed. The techniques for administering these materials to animals are known to those skilled in the veterinary field.

When the compound described herein is administered as a component of the feed of the animals, or dissolved or suspended in the drinking water, compositions are provided in which the active compound is intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typically carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compound is intimately dispersed throughout the carrier by methods such as grinding, stirring, milling or tumbling. Compositions containing about 0.005 to 2 0% by weight of the active compound are particularly suitable as feed premixes. Feed supplements, which are fed directly to the animal, contain from about 0.0002 to 0.3% by weight of the active compound.

Such supplements are added to the animal feed in an amount to give the finished feed the concentration of active compound desired for the treatment and control of parasitic diseases. Although the desired concentration of active compound will vary depending upon the factors previously mentioned, the instant compound is usually fed at concentrations of between 0.0001 to 0.02% in the feed in order to achieve the desired antiparasitic result.

The compound of this invention has a broad spectrum of activity against many internal parasites at low dosage levels and in many different animals. At levels of about 5 mg per kg of animal body weight, concentrated mixtures of the instant compound are fully active in sheep against Fasciola In rodents, such as mice, infections of Fasciola hepatica have been successfully treated by the oral administration of the instant compound or of the concentrates obtained from the extraction of the fungal mycelia.

The instant compound is also useful in combatting agricultural pests that inflict damage upon crops while they are growing or while in storage. The compound is applied using known techniques as sprays, dusts, emulsions and the like, to the growing or stored crops to effect protection from such agricultural pests.

It is especially useful in animals against ectoparasites such as *Lucilia sericata* and has the additional advantage of being useful against endoparasitic helminths such as *Fasciola hepatica* which can infect humans, animals and plants.

Xanthomegnin may be administered orally, topically, or parenterally in dosage unit formulations containing conventional non-toxic pharmaceutically acceptable carriers, adjuvants and vehicles. The term parenteral as used herein includes subcutaneous inJections, intravenous, intramuscular, intrasternal injection or infusion techniques.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets containing the active ingredient in admixture with non toxic pharmaceutically acceptable excipients may also be manufactured by known methods. The excipients used may be for example, (1) inert diluents such as calcium carbonate, lactose, calcium Phosphate or sodium phosphate; (2) granulating and disintegrating agents such as corn starch, or alginic acid; (3) binding agents such as starch, gelatin or acacia, and (4) lubricating agents su:h as magnesium stearate, stearic acid or talc. The tablets may be uncoated or they may be coated by known techniques to delay intestinal tract absorption and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example Peanut oil, liquid paraffin, or olive oil.

Aqueous suspensions normally contain the active material in admixture with excipients suitable for the manufacture of aqueous suspensions Such excipients may be:

(1) suspending agents such as sodium carboxymethyl:cellulose, methylcellulose, hydroxypropylmethylcellulose, sodium alginate, polyvinyl pyrrolidone, gum tragacanth and gum acacia;

(2) dispersing or wetting agents which may be:

(a) a naturally-occuring phosphatide such as lecithin, (b) a condensation product of an alkylene oxide with a fatty acid, for an example, polyoxyethylenestearate, (c) a condensation product of ethylene oxide with a long chain aliphatic alcohol, for example, heptadeca-ethyleneoxycetanol, (d) a condensation product of ethylene oxide with a partial ester derived from a fatty acid and hexitol such as polyoxyethylene sorbitol monooleate, or (e) a condensation product of ethylene oxide with a partial ester derived from a fatty acid and a hexitol anhydride, for example polyoxyethylene sorbitan monooleate.

These aqueous suspensions may also contain one or more preservatives, for example, ethyl or n-propyl p-hydroxybenzoate; one or more coloring agents; one or more flavoring agents., and one or more sweetening agents such as sucrose or saccharin.

Oily suspensions may be formulated by suspending the active ingredient in a vegetable oil, for example arachis oil, olive oil or coconut oil, or in a mineral oil su:h as liquid paraffin. The Oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oil, or a mineral oil such as liquid paraffin or a mixture thereof. Suitable emulsifying agents may be (1) naturally-occuring gums such as gum acacia and gum tragacanth, (2) naturally-occuring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Xanthomegnin may also be administered in the form of suppositories for rectal administration of the drug. These compositions can be prepared by mixing the drug with a suitable non irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the active ingredient are employed.

The amount of active ingredient that may be combined with the carrier materials to produce a single dosage form will vary depending upon the host treated and the particular mode of administration. For example, a formulation intended for the oral administration of humans may contain 0.001 mg to 100 mg of an active compound with an appropriate and convenient amount of carrier material which may vary from about 5 to about 95 percent of the toal composition. Dosage unit forms will generally contain between from about 0.001 mg to about 100 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples are being provided in order that the instant invention may be more fully understood. The following examples illustrate the invention but are not to be construed as limiting.

EXAMPLE 1

Fermentation broths containing xanthomegnin were mixed at various dose levels (0.0,ml, 3.8 ml, 4.5 ml, and 21ml) with standard laboratory mouse chow, and fed to female Charles River CD-1 mice ad libitum for 5 days. The total dose of xanthomegnin was between about 0.1 and 100 mg/kg/mouse. On the fifth day the mice were sacrificed and 0.75 milliliters of blood was collected via syringe from the inferior vena cava of each mouse. The blood was absorbed into sterile dental cotton in 17 × 60 millimeter shell vials. Five one-day old *Lucilia sericata* larvae were introduced onto the blood saturated dental cotton. The vials were stoppered and incubated at 82° F. until termination of the experiment. The vials were examined daily. As a control for normal growth and development, 21 larvae were raised on nontreated mouse blood. Normally, *Lucilia sericata* larvae develop into pupae from which adult flies emerge. The results are shown in the following table:

TABLE I

| Treatment | Volume of fermentation broth in chow[1] | Input # of larvae | # Pupae Day: 7 | 8 | 9 | # Adult Flies Day: 12 | 13 | 14 |
|---|---|---|---|---|---|---|---|---|
| None | — | 21 | 13 | 13 | 21 | 5 | 20 | 20 |
| Fermentation 1 | 21.0 ml | 5 | 0 | 0 | 0 | 0 | 0 | 1* |
| Fermentation 2 | 4.5 ml | 5 | 0 | 0 | 1 | 0 | 0 | 0 |
| Fermentation 3 | 3.8 ml | 5 | 0 | 1 | 3 | 0 | 0 | 0 |

*abnormally developed
[1]The fermentation broth contained about 0.4 mg/ml xanthomegnin.

This experiment demonstrates the ability of xanthomegnin, administered through the diet and present in the blood, to inhibit the growth and development of the larvae of *Lucilia sericata*. Such inhibition prevents the development of adult flies and interrupts the life cycle of the parasite, demonstrating the antiparasitic, insecticidal activity of xanthomegnin.

EXAMPLE 2

A fermentation broth containing xanthomegnin was mixed at various dose levels (0.0 ml, 10.0 ml, and 23.0 ml with standard laboratory mouse chow and fed, ad libitum, for up to 21 days to mice previously infected with *Fasciola hepatica*. The total dose of xanthomegnin was between about 0.1 and 100mg/kg/mouse. In *Fasciola hepatica* infected mice, numerous liver flukes are normally present and have a typical morphology. An infected, unmedicated mouse was used as a control. Following the treatment period the mice were sacrificed. At necropsy the mouse livers were examined to determine the condition of the *Fasciola heratica* flukes. The results are summarized in the following table.

TABLE II

| Treatment | Volume of fermentation broth in chow[1] | Fluke condition |
|---|---|---|
| None | — | Normal fluke |
| Fermentation broth A | 23 ml | all dead fluke |
| Fermentation broth A | 10 ml | all dead fluke |

[1]The fermentation broth contained about 0.4 mg/ml xanthomegnin.

This experiment demonstrates the ability of xanthomegnin, administered through the diet, to kill the liver fluke *Fasciola hepatica* in vivo, in experimentally infected mice. The demonstrated toxicity toward *Fasciola hepatica* eliminated the infection in mice, demonstrating the antiparasitic, anthelminthic activity of xanthomegnin.

What is claimed is:

1. A method for treating animals infected or infested with helminths, acarids, or insects which comprises treating the animal or area infected or infested with helminths, acarids, or insects with an effective amount of xanthomegnin.

2. The method according to claim 1 wherein from about 0.1 mg xanthomegnin/kilogram body weight to about 100 mg xanthomegnin/kilogram body weight is administered.

* * * * *